US007717929B2

(12) United States Patent
Fällman

(10) Patent No.: US 7,717,929 B2
(45) Date of Patent: May 18, 2010

(54) TECHNIQUE FOR SECURING A SUTURE

(75) Inventor: David Fällman, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 438 days.

(21) Appl. No.: 11/694,496

(22) Filed: Mar. 30, 2007

(65) Prior Publication Data

US 2007/0239209 A1 Oct. 11, 2007

Related U.S. Application Data

(63) Continuation-in-part of application No. 10/805,486, filed on Mar. 22, 2004.

(60) Provisional application No. 60/530,618, filed on Dec. 19, 2003.

(51) Int. Cl.
*A61B 17/08* (2006.01)
(52) U.S. Cl. ..................... 606/158; 606/215
(58) Field of Classification Search ............ 606/151, 606/158, 213, 215, 216, 228, 232; 57/22; 87/6, 8
See application file for complete search history.

(56) References Cited

U.S. PATENT DOCUMENTS

| 5,062,344 | A | 11/1991 | Gerker | |
|---|---|---|---|---|
| 5,540,703 | A | * 7/1996 | Barker et al. | ............... 606/139 |
| 5,683,417 | A | 11/1997 | Cooper | |
| 6,296,659 | B1 | * 10/2001 | Foerster | ................... 606/224 |
| 6,425,911 | B1 | 7/2002 | Akerfeldt et al. | |
| 6,503,267 | B2 | 1/2003 | Bonutti et al. | |
| 6,508,828 | B1 | 1/2003 | Akerfeldt et al. | |
| 6,746,472 | B2 | 6/2004 | Frazier et al. | |
| 6,929,655 | B2 | 8/2005 | Egnelov et al. | |
| 7,025,756 | B2 | 4/2006 | Frazier et al. | |
| 7,150,757 | B2 | 12/2006 | Fallin et al. | |
| 2002/0029066 | A1 | 3/2002 | Foerster | |
| 2002/0161168 | A1* | 10/2002 | Shalaby et al. | ............. 528/310 |
| 2004/0093025 | A1 | 5/2004 | Egnelov | |
| 2004/0138674 | A1 | 7/2004 | Egnelov et al. | |
| 2004/1013858 | | 7/2004 | Egnelov et al. | |

* cited by examiner

*Primary Examiner*—Todd E Manahan
*Assistant Examiner*—Katherine M Dowe
(74) *Attorney, Agent, or Firm*—Foley & Lardner LLP

(57) ABSTRACT

A device to seal an incision in a blood vessel includes an inner member and an outer member. A suture connects the inner member and the outer member. A first portion of the suture is embedded within a second portion of the suture such that as tension in the suture increases the first and second portions are held together. According to certain embodiments, the second portion is not part of a first suture portion, and both the first and second portions are used to retain the outer member in place. A method of making such a device is also described.

17 Claims, 8 Drawing Sheets

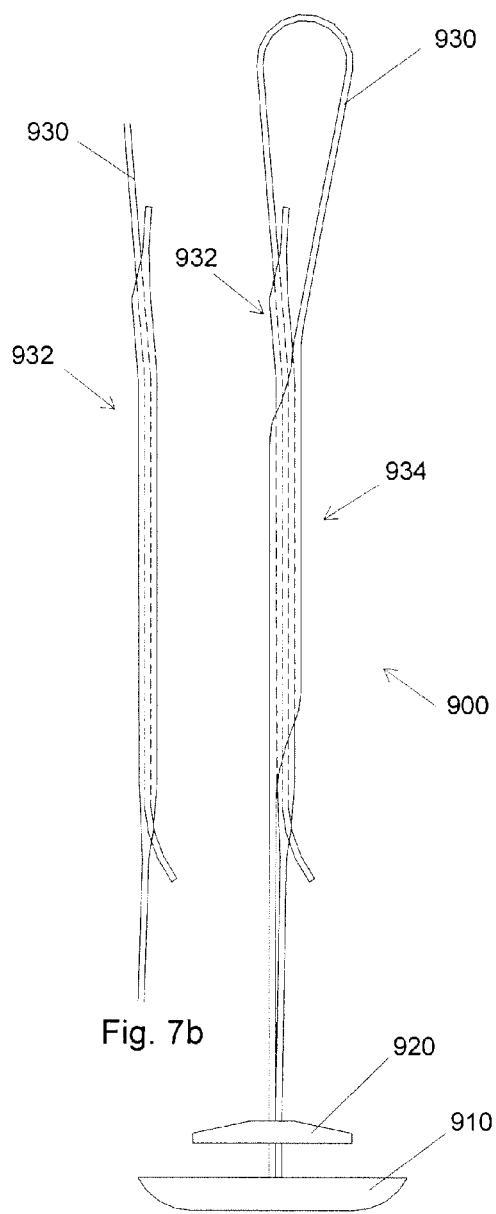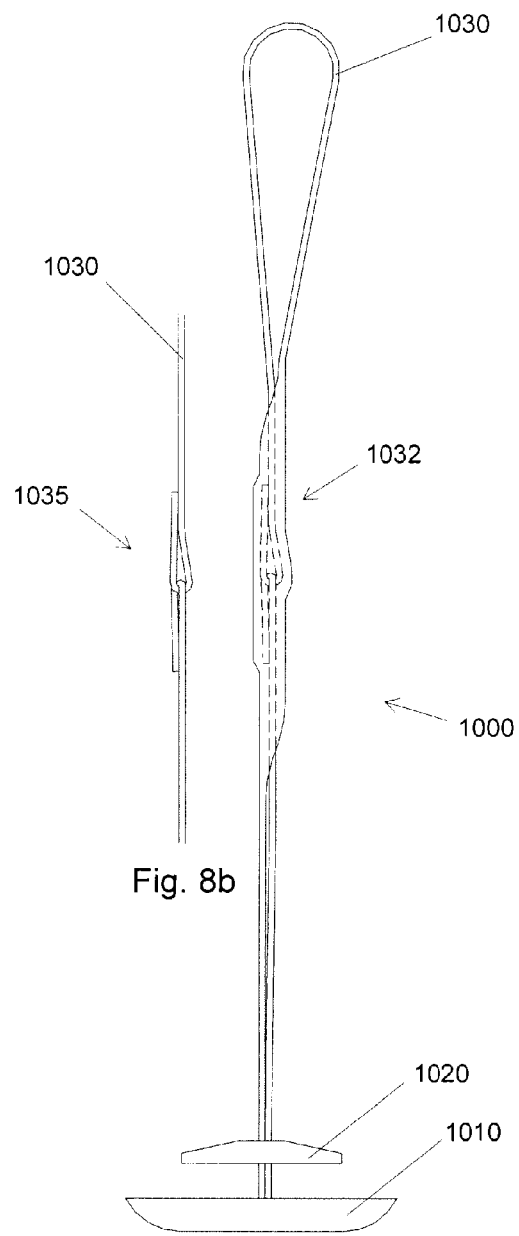
Fig. 7a  Fig. 7b  Fig. 8a  Fig. 8b

TECHNIQUE FOR SECURING A SUTURE

CROSS-REFERENCE TO RELATED PATENT APPLICATIONS

This application is a continuation-in-part of U.S. application Ser. No. 10/805,486, filed Mar. 22, 2004, which in turn claims the benefit of U.S. Provisional Application No. 60/530,618, filed Dec. 19, 2003. The entire contents of both of these applications are incorporated herein by reference.

BACKGROUND OF THE INVENTION

There are several medical procedures which require access to a patient's vascular system. Access to a patient's vascular system can be provided by making an incision (sometimes called a puncture, wound, or hole) in an artery (or other blood vessel) below the skin surface. At the conclusion of the medical procedure, the incision in the artery must be sealed.

One technique for sealing such an incision is to place an inner seal within the artery and an outer locking element outside the artery in such a fashion as to seal the incision. The seal is made of bioabsorbable materials which are absorbed within the body over time. The inner seal, the outer locking element, and the suture are usually components of an introducer and sealing assembly. A suture loop is needed to guide and hold the seal, the locking element, and the suture during the sealing procedure. The suture (for example, a thread or a multifilament fiber) holds the inner seal in place and guides the locking element to a position outside of the artery opposite the inner seal. Typically, in such a suture loop, the ends (or other portions) of the suture are glued or tied together to complete the loop.

Similar suture loops can also be used when a closure comprises an inner anchor member and an outer seal, e.g., in the form of a collagen plug, which are held together by a suture loop, or when an outer member and an inner member are clamped together to thereby seal a puncture in an intermediate blood vessel wall.

Additional background on the techniques described above is set forth in U.S. Pat. Nos. 6,508,828 and 6,425,911, and U.S. patent applications Ser. Nos. 10/280,086, 10/341,599, and 10/341,598, whose entire contents are incorporated herein by reference.

SUMMARY OF THE INVENTION

It has been discovered that the use of glue or knot(s) to form the loop has disadvantages. For example, the use of glue in the manufacturing process complicates manufacturing because the glue has to be applied properly, has to be immobilized while drying, etc. Knot(s) reduce the strength of a suture, and make the overall design more complicated because care must be taken to make sure that the knot(s) pass through various components (e.g., components of an introducer device used to guide and push the sealing and/or locking members in place during a sealing procedure).

The present invention provides a technique to connect the ends (or other portions) of a suture used in sealing an incision in a blood vessel. In the present invention, portions of the suture are joined together (for example, to form a loop) by embedding one portion of the suture within another portion of the suture, such that as tension in the suture increases, the different portions of the suture are held together. This joining may be accomplished using a needle, by sticking a suture into itself, by a splice, by weaving, by embedding, or by any other technique wherein tension in the suture maintains or increases the holding power.

The tension in the suture contracts (i.e., reduces the cross-sectional area of) the suture such that the friction force between the walls of the suture portions (i.e., between a first portion and a second portion, which is enclosed by the first portion) increases and becomes larger than the force (tension) that tries to separate the portions (i.e., larger than the force pulling the two portions apart).

According to certain embodiments of the invention, the invention is applied to a device used to close an incision having an inner member, an outer member, and a first suture connected to the inner member and the outer member. At least one other suture portion, which is not part of the first suture, is embedded in a portion of the first suture to retain the outer member in place when the outer member is slid over the at least one other suture portion and the portion of the first suture.

A method of making such a device includes threading a first suture through the inner member and providing a second suture which is not part of the first suture. At least one suture portion of the second suture is embedded in a portion of the first suture, to enlarge an outer dimension of the first suture to a configuration such that an outer member is retained in place when the outer member is slid over the at least one suture portion of the second suture and the portion of the first suture. The second suture is cut to shorten the second suture.

BRIEF DESCRIPTION OF THE DRAWINGS

Preferred embodiments of the invention are shown in the drawings wherein:

FIGS. 7(a) to 14 illustrate sixth to twelfth embodiments of the invention.

DETAILED DESCRIPTION OF THE PREFERRED EMBODIMENTS

Figure 1:
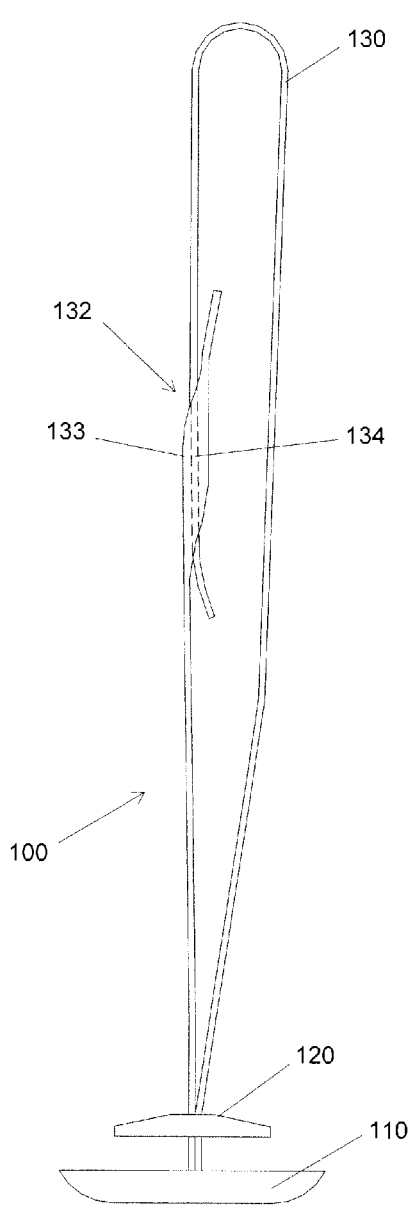
FIG. 1 illustrates one embodiment of the invention wherein a suture is embedded in itself.

FIG. 1 illustrates a first preferred embodiment 100. As shown in FIG. 1, first preferred embodiment 100 includes an inner seal 110, an outer locking element 120, and a suture 130. The suture 130 has a portion 132 wherein a first portion 134 of the suture is embedded in a second portion 133 of the suture, as shown in FIG. 1. In this manner, as tension in the suture increases, the portions 133 and 134 are held together due to portion 133 contracting (in cross section) and exerting friction on portion 134.

Figure 2A:
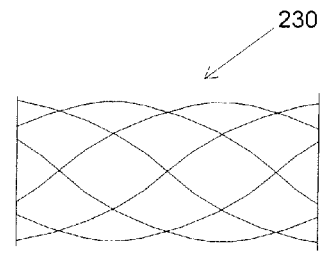
FIGS. 2a to 2d illustrate various sutures suitable for use in the invention.
Figure 2B:
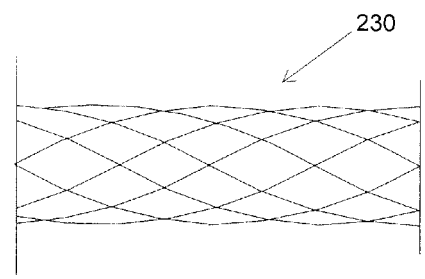
Figure 2C:
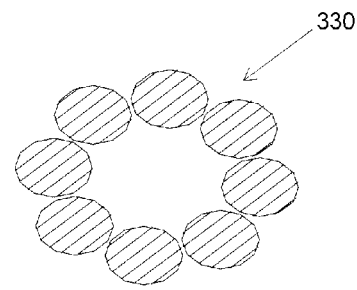
Figure 2D:
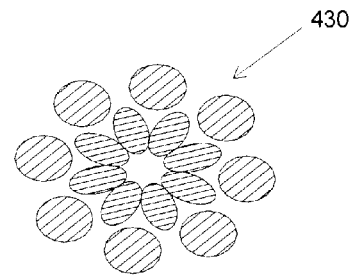

FIGS. 2a to 2d illustrate some examples of sutures which may be employed in the present invention. FIG. 2a shows a suture 230 in a relaxed state and FIG. 2b shows the same suture 230 in a state of tension. FIG. 2c illustrates a suture 330 having a single layer of filaments and FIG. 2d shows a suture 430 having two layers of filaments. Other suture designs may be used in the invention.

Figure 3:
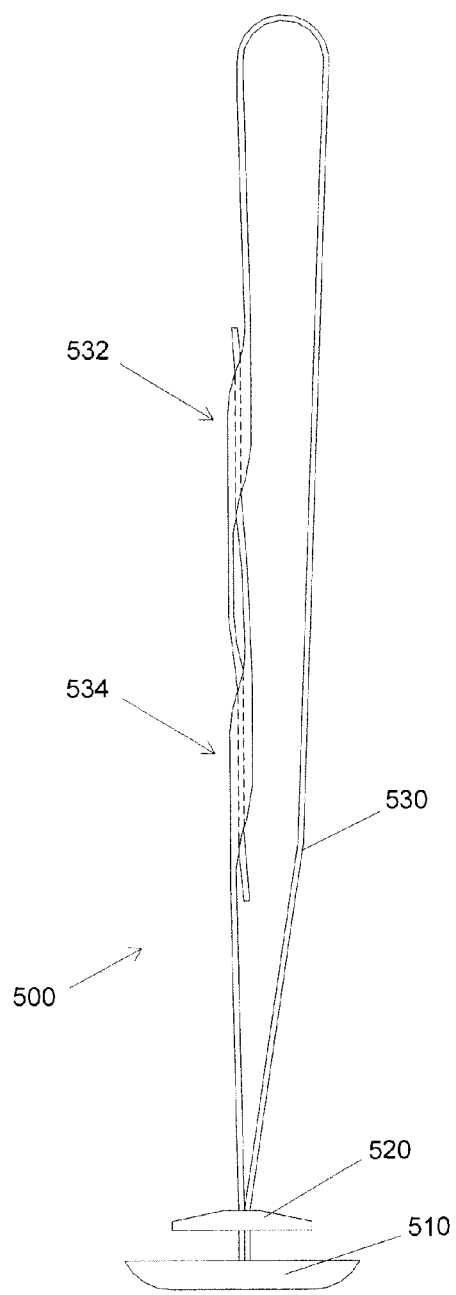
FIGS. 3 and 4 illustrate second and third embodiments of the invention wherein the suture is embedded in itself at multiple places for additional strength.

FIG. 3 illustrates a second embodiment 500. The second embodiment includes an inner seal 510 and a locking element 520. A suture 530 is used to connect inner seal 510 and locking element 520. In the second embodiment, there are two portions 532 and 534 wherein one portion of the suture is embedded within another portion of the suture such that as tension in the suture increases, the portions are held together. The second embodiment has the advantage over the first embodiment of additional strength.

Figure 4:
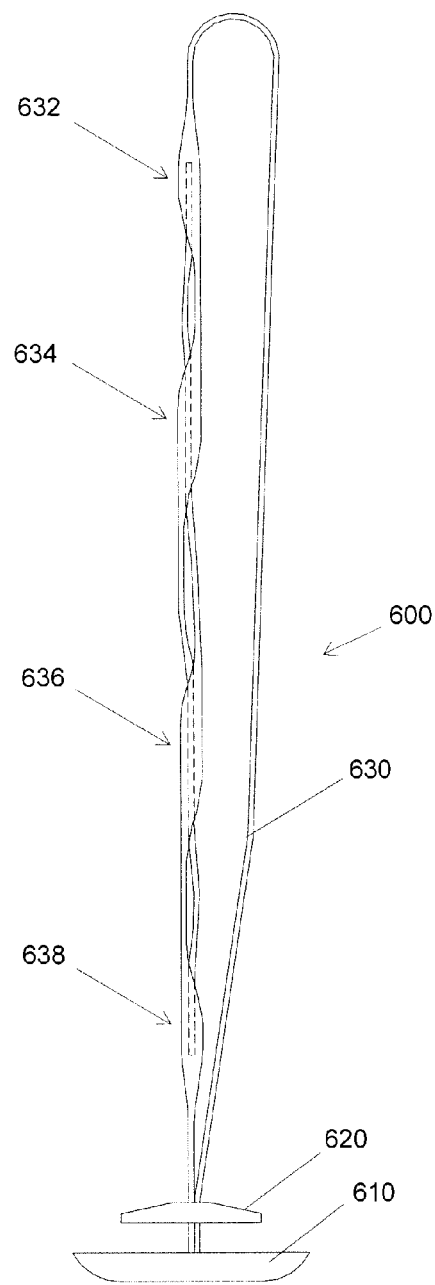

FIG. 4 illustrates a third embodiment 600 which includes an inner seal 610, a locking element 620, and a suture 630. The third embodiment 600 includes four portions 632, 634, 636, and 638 wherein one portion of the suture is embedded within another portion of the suture. In FIG. 4, the end portions of the suture have been embedded into the suture such that there are no portions that stick out and thus no portions that can get stuck during a sealing procedure.

Figure 5:
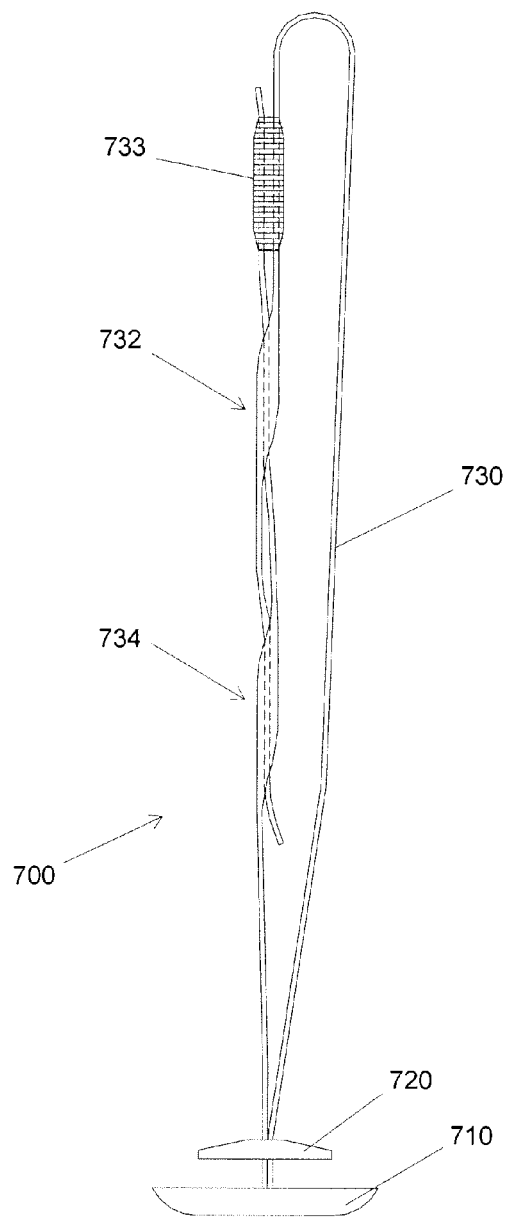
FIGS. 5 and 6 illustrate fourth and fifth embodiments which are similar to FIGS. 3 and 4 except that glue is also used to join the sutures in FIGS. 5 and 6.

FIG. 5 illustrates a fourth embodiment which includes an inner seal 710, a locking element 720, and a suture 730. In this fourth embodiment 700, two portions 732 and 734 are provided wherein a part of the suture is embedded within another part of the suture. The embodiment 700 also includes glue 733 which is used to fashion two portions of the suture together for added strength.

Figure 6:
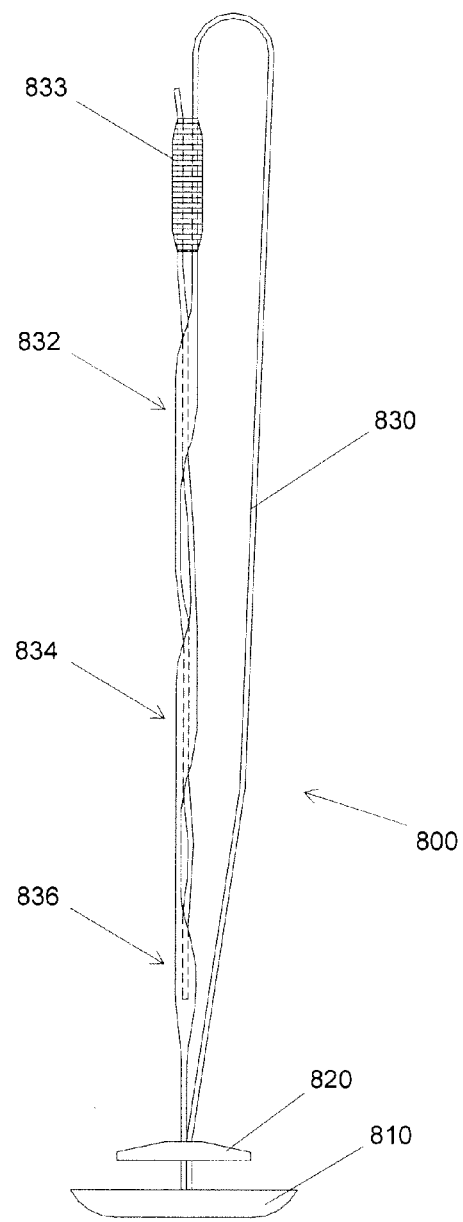

FIG. 6 illustrates a fifth embodiment 800 which includes an inner seal 810, a locking element 820, and a suture 830. Three portions 832, 834, and 836 are provided wherein one portion of the suture is embedded within another portion of the suture. The embodiment 800 also utilizes glue 833, similar to the fourth embodiment. In FIG. 6, one end portion of the suture is embedded into the suture and the other end portion is secured by glue at or near the end such that there are no portions that stick out and no portions that can get stuck.

FIGS. 7a and 7b illustrate a sixth embodiment 900 which includes an inner seal 910, a locking element 920, and a suture 930. As shown in FIG. 7b (which illustrates a part of the arrangement of FIG. 7a, with other parts removed for clarity), the sixth embodiment 900 includes a portion 932 wherein one portion of the suture is embedded in another portion of the suture. As illustrated in FIG. 7a, this portion 932 is itself embedded within an additional portion 934.

FIGS. 8a and 8b illustrate a seventh embodiment 1000, which includes an inner seal 1010, a locking element 1020, and a suture 1030. As shown in FIG. 8b (which illustrates a part of the arrangement illustrated in FIG. 8a, with other parts removed for clarity), the ends of the suture are looped around one another in an arrangement 1035. The arrangement 1035 is in turn embedded within a portion 1032 of the suture 1030.

Figure 9:
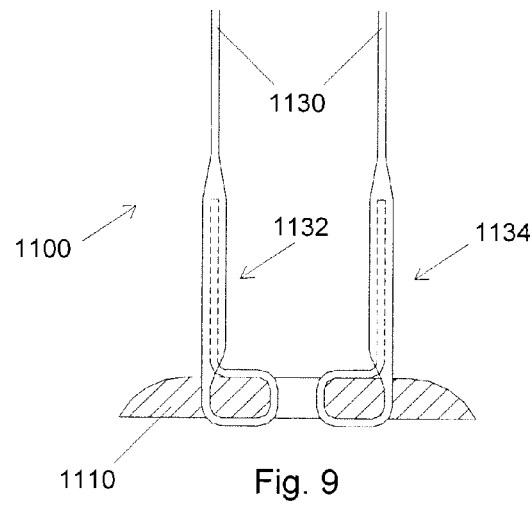
Figure 10:
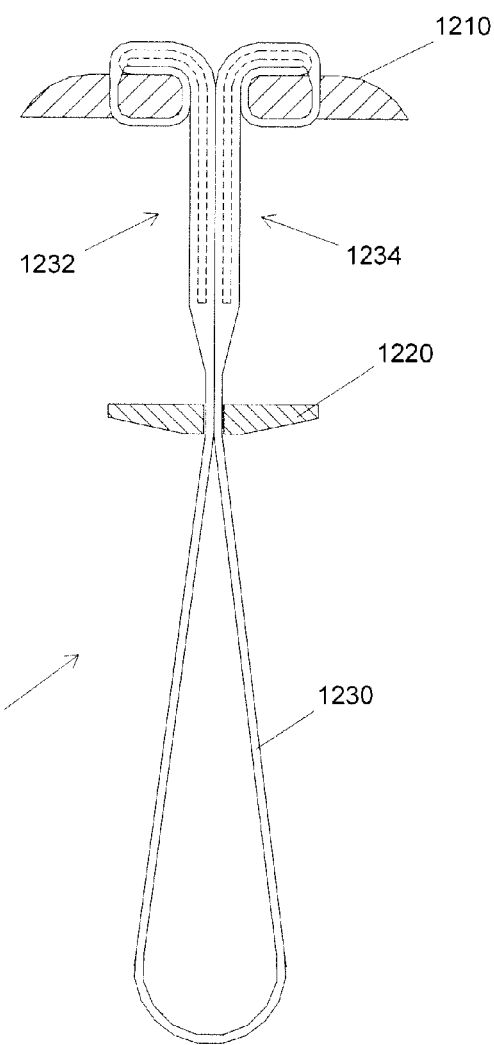

FIG. 9 illustrates an eighth embodiment 1100 which is used to connect an inner seal 1110 to a suture 1130. In the eighth embodiment 1100, the ends of the suture are looped around seal 1110 and then embedded into the suture at portions 1132 and 1134. FIG. 10 illustrates a ninth embodiment 1200, which includes an inner seal 1210, an outer locking element 1220, and a suture 1230. In this embodiment, the ends of suture 1230 are embedded into portions of the suture 1232 and 1234. In FIGS. 9 and 10, an enlarged cross-section created by the present way of joining portions of the suture is utilized to hold the inner seal and/or locking element in place by friction. In other words, the enlarged portions 1132, 1134, 1232, and 1234 can retain the locking element (e.g., locking element 1220) in place when the locking element is slid over these portions. A portion of the loop which has an enlarged thickness could be used to hold an outer member (or other member) in place by friction in the other embodiments. For example, the FIG. 7 embodiment could be modified to hold the outer member by placing the enlarged portion close to the inner member and adjusting the resilience and diameter of the hole in the outer member accordingly.

Figure 11:
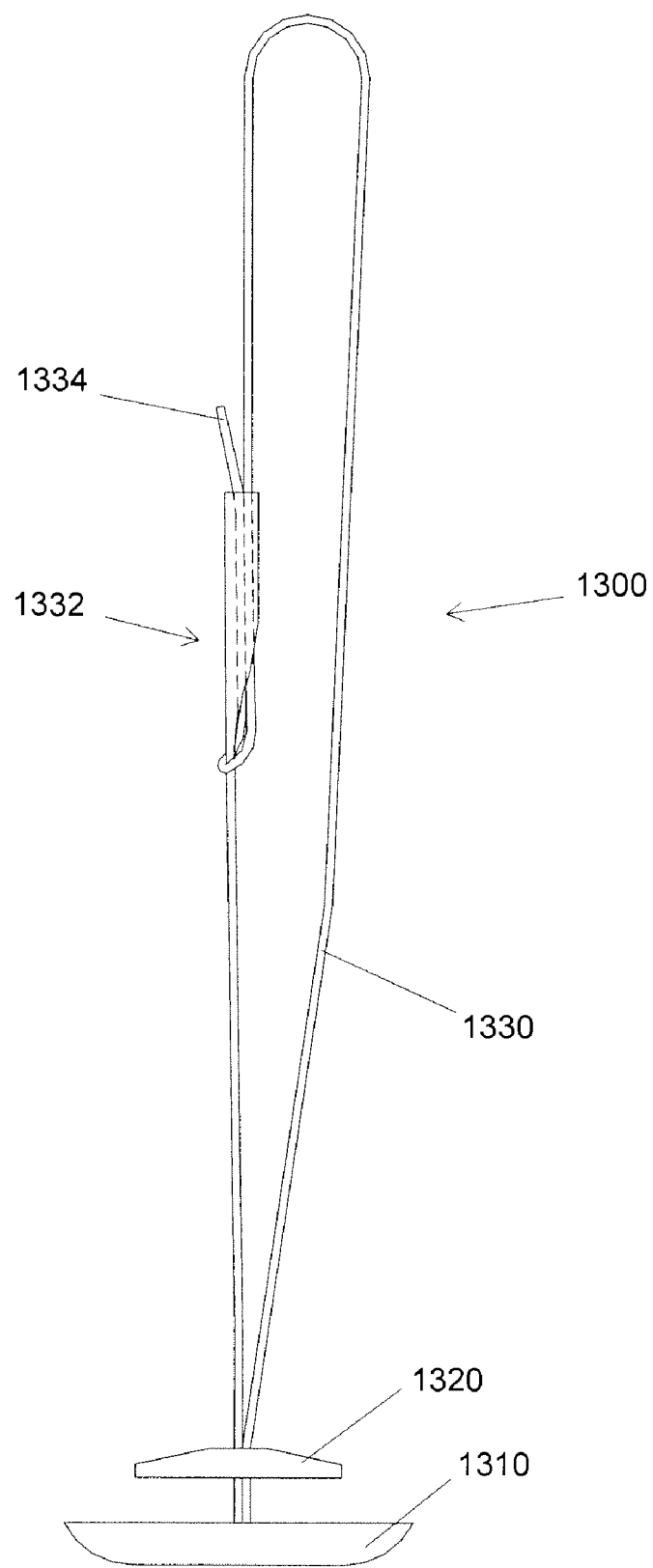

FIG. 11 illustrates a tenth embodiment 1300, which includes an inner seal 1310, a locking element 1320, and a suture 1330. In this embodiment, one end 1334 of suture 1330 is wrapped around the suture and then embedded in another portion of the suture, as shown in FIG. 11.

A common feature of the previously described embodiments is that the suture embedding technique is utilized as a way of joining two suture portions, typically of one and the same suture. This is in particular true also for the embodiments shown in FIGS. 7, 9 and 10, respectively, wherein the resulting joined portion, which has an enlarged thickness, is exploited as a friction lock for an outer member of a closure device. In the prior art it is known to create a friction lock by an elongated core, preferably made from a resorbable polymer, e.g. caprolactone/trimethylene carbonate/glycolide polymer, as suggested in the U.S. Pat. No. 6,508,828, which is assigned to the present assignee and the contents of which are incorporated herein by reference.

The inventor has discovered that creating a friction lock by a suture embedding technique—instead of using a separate core—provides certain advantages. From a manufacture point of view it is easier to thread a first suture into a second suture (which can be done using a needle) than to insert a separate core into a suture. When in place, the embedded suture creates a smooth and compliant transition from a thin suture portion to thick suture portion for an outer member, which is pushed up and over the enlarged diameter portion, whereas a separate core is more unresilient and "unforgiving". Care has also to be taken to ensure that the core does not creep out of the suture after it has been implanted. It may further be noted that in the U.S. Pat. No. 6,508,828 arrangement two different materials are suggested for the core and the suture, namely glycolide/lactide polymer and caprolactone/trimethylene carbonate/glycolide polymer, respectively, implying that the two members will exhibit different properties regarding, for example, resorption time. To have the same resorption time for different components is usually advantageous for a resorbable medical device.

However, when a suture embedding technique is utilized for creating a multi-functional joint, which besides serving as a joint of two suture portions also constitutes a friction lock for an outer member of a closure device, the resulting joined portion must possess a certain length, i.e. the length of the first suture portion which is embedded in the second suture portion cannot be too short. When the joining portion also is used as a friction lock, this requirement must be compatible with other requirements originating from the design of an insertion tool, by which the closure device is to be deployed at a vessel wall. A multi-functional suture joint may therefore have some disadvantages from a manufacturing point of view.

Figure 12:
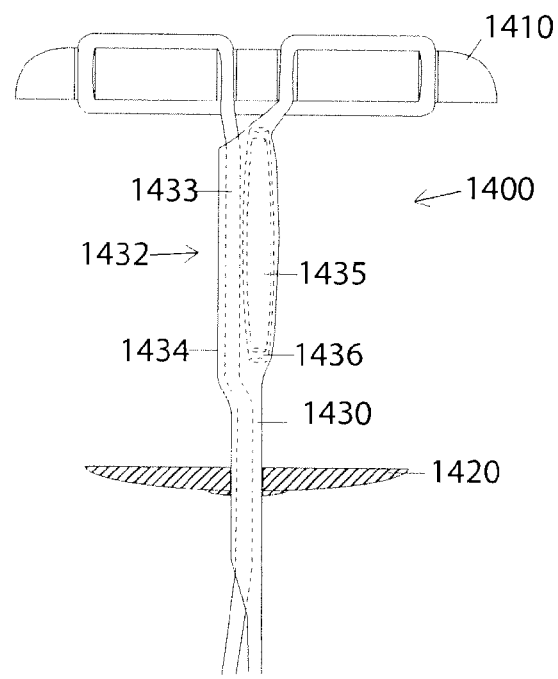

FIG. 12 illustrates an eleventh embodiment 1400 of the present invention, where an inner member 1410 is connected to a suture 1430, which has a portion 1432, wherein a first portion 1433 of the suture 1430 is embedded in a second portion 1434 of the suture 1430, similar to the technique that previously has been described in conjunction with, for example, the first embodiment illustrated in FIG. 1. In contrast to the embodiments above, the portion 1432 comprises, however, two further suture portions 1435 and 1436. In this particular example, suture portion 1435 is embedded in suture portion 1436, to contribute to the total thickness of the portion 1432, which serves as a friction lock for an outer member 1420. In FIG. 12, the outer member 1420 is shown in a state before it is pushed up and over portion 1432. It is within the scope of the present invention to use only one extra suture portion, like suture portion 1435 or suture portion 1436, to create the friction lock portion 1432, or to use more than two suture portions to create an even thicker friction lock portion. Once again it should be emphasized that in the eleventh embodiment 1400 of the present invention, the friction lock portion 1432 partly is created by the suture portions 1435, 1436, which are not parts of the main suture 1430. The last feature is in contrast to the embodiments described above. The extra suture portion comprising sutures 1435 and 1436 is made independently of the main suture 1430 and is threaded (by use of a needle) into the suture 1430 at portion 1432. Not visible in FIG. 12, the end portions of the main suture 1430 may or may not be joined together by a suture embedding technique, as previously have been described, or may be joined by some other technique, like by a simple knot or by gluing.

Figure 13:
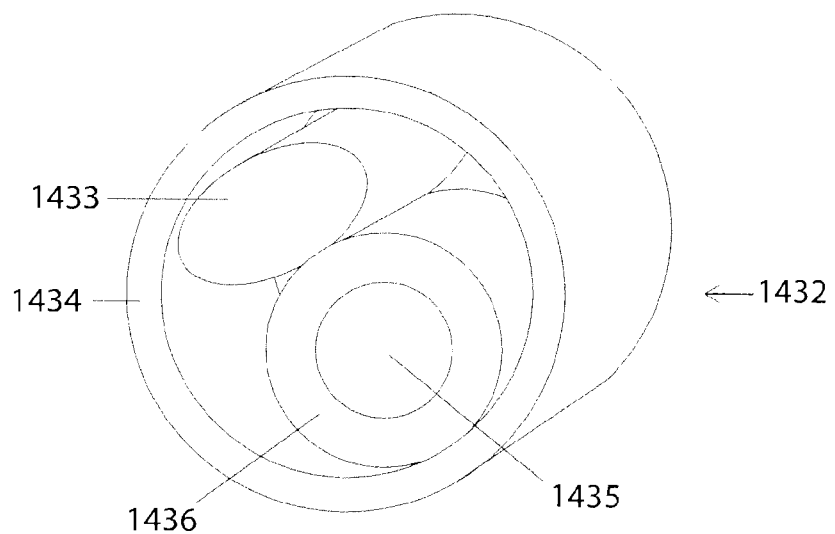

In FIG. 13 a cross-section of the friction lock portion 1432 is schematically depicted, and illustrates that the suture portion 1435 is embedded in the suture portion 1436 to contribute to the total thickness of the friction lock portion 1432. The suture portion 1433 is positioned adjacent the suture portions 1435 and 1436; and the suture portions 1433, 1435 and 1436 are all disposed inside the suture portion 1434. As stated above, the suture portions 1433 and 1434 are both parts of the same suture 1430, whereas suture portions 1435 and 1436 are not parts of the suture 1430. The suture portions 1435, 1436 can, however, be made from the same suture material as suture 1430, such that all suture portions exhibit the same physical properties regarding, for example, the resorption time.

Figure 14:
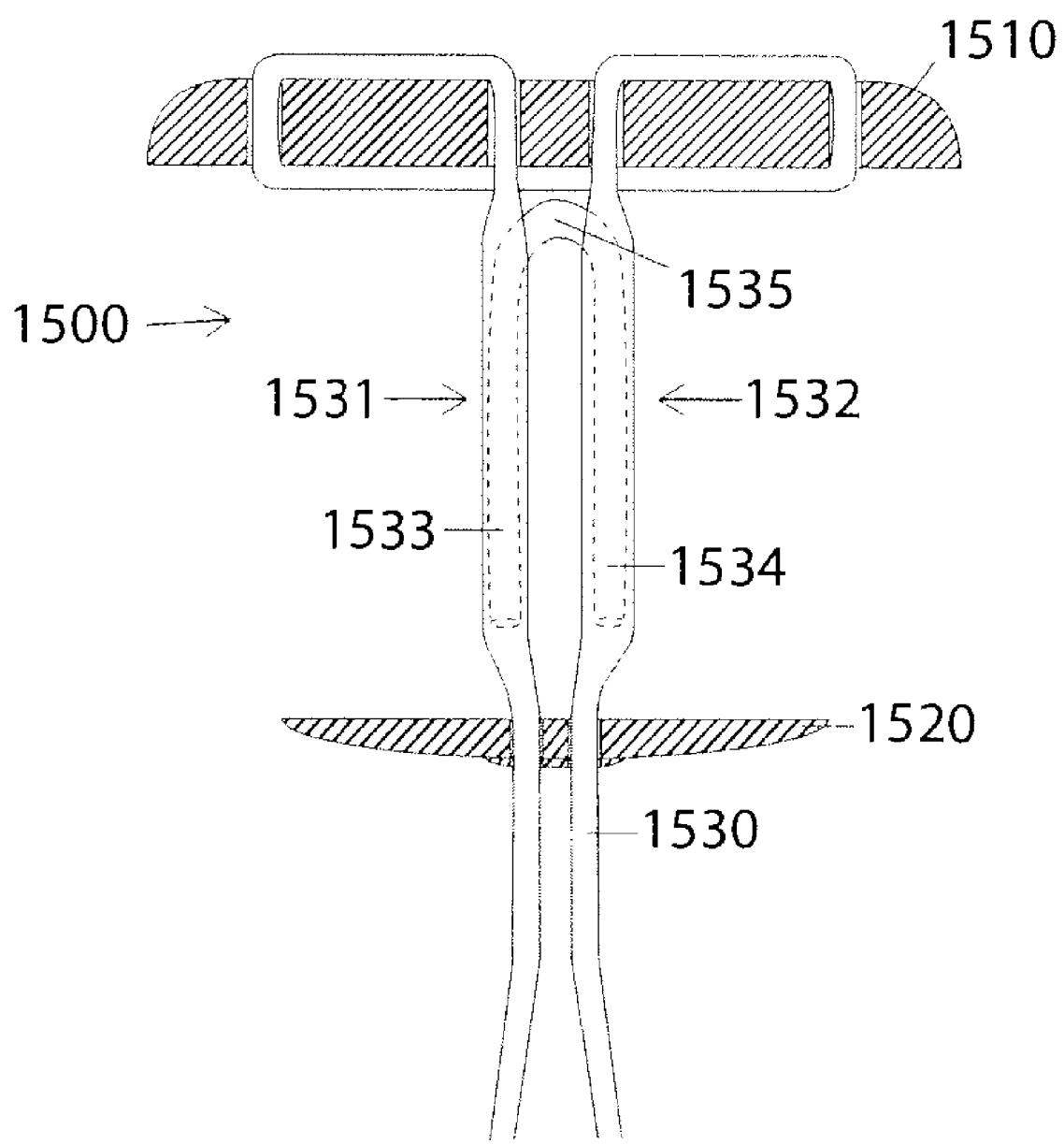

FIG. 14 shows a twelfth embodiment 1500 of the present invention, where an inner member 1510 is connected to a first suture 1530, which comprises a first portion 1531 and a second portion 1532. Inside the first portion 1531 of the suture 1530, a first portion 1533 of a second suture 1535 has been embedded, and a second portion 1534 of the second suture 1535 is embedded in the second portion 1532 of the first suture 1530. The first and second portions 1533, 1534 of the second suture 1535 thereby contribute to the thicknesses of the first and second portions 1531 and 1532, which serve as friction locks for an outer member 1520. Like in the eleventh embodiment of FIG. 12, the friction lock portions 1531, 1532 are made from a second suture 1535, which is separate from the main suture 1530. The friction lock portions can be made from any number of sutures which are threaded into each other, or from suture portions having a thickness larger than the thickness of the main suture 1530. It can also be noted that in the embodiment of FIG. 14, the outer member 1520 has been provided with two through holes, and consequently two friction lock portions 1531, 1532 have been provided.

In the foregoing description, it should be understood that the term "suture" is meant to encompass all types of threads and filaments, including multi-filaments, which, within the medical field, are used to connect inner and outer members of a sealing or closure device.

The foregoing description of preferred embodiments of the invention has been presented for purposes of illustration. It is not intended to be exhaustive or to limit the invention to the precise form disclosed, and modifications and variations are possible in light of the above teachings. It is intended that the scope of the invention be defined with reference to the claims appended hereto, and their equivalents.

What is claimed is:

1. A device to close an incision, comprising:
    an inner member;
    an outer member; and
    a first suture connected to the inner member and the outer member, wherein a first portion of said first suture is embedded within a second portion of said first suture;
    at least one suture portion of a second suture, which is embedded in said second portion of said first suture along a length of and adjacent to said first portion of the first suture, to retain the outer member in place when the outer member is slid over said at least one suture portion of said second suture and said first portion of the first suture, wherein said at least one suture portion of said second suture is not part of the first suture, wherein the at least one suture portion of the second suture is a multifilament suture.

2. A device as set forth in claim 1, wherein the first suture and said at least one suture portion of said second suture are made from the same material.

3. A device as set forth in claim 1, wherein the first suture comprises a multifilament suture.

4. A device as set forth in claim 1, wherein both ends of said at least one suture portion of said second suture are substantially enclosed by the first suture.

5. A device as set forth in claim 1, further comprising a third suture portion which is embedded in said second portion of the first suture.

6. A device as set forth in claim 1, wherein said at least one suture portion of said second suture and said first suture exhibit substantially the same physical properties.

7. A device as set forth in claim 1, wherein said at least one suture portion of said second suture and said first suture exhibit substantially the same resorption time.

8. A device as set forth in claim 1, wherein the inner member and outer member are configured to seal an incision in a blood vessel.

9. A device as set forth in claim 1, wherein said at least one suture portion of said second suture is a separate suture that is not part of any other suture of said device.

10. A device as set forth in claim 1, wherein said at least one suture portion of said second suture is completely embedded in said second portion of said first suture such that no portion of said at least one suture portion of said second suture is visible.

11. A device as set forth in claim 1, wherein said first portion of said first suture and said at least one suture portion of said second suture do not contact the outer member.

12. A method of making a device to close an incision, comprising:
    providing an inner member;
    threading a first suture through the inner member;
    embedding a first portion of said first suture within a second portion of said first suture providing a second suture which is not part of the first suture;
    using a needle to thread at least one suture portion of said second suture through said second portion of said first suture to embed said at least one suture portion of said second suture along a length of and adjacent to said first portion of said first suture within said second portion of said first suture, to enlarge an outer dimension of the first suture to a configuration such that an outer member is retained in place when the outer member is slid over said at least one suture portion of said second suture and said first portion of the first suture; and
    cutting the second suture to shorten the second suture, wherein the at least one suture portion of the second suture is a multi-filament suture.

13. A method as set forth in claim 12, wherein both ends of said at least one suture portion of said second suture are substantially enclosed by the first suture.

14. A method as set forth in claim 12, wherein the inner member and outer member are configured to seal an incision in a blood vessel.

15. A method as set forth in claim 12, wherein said at least one suture portion of said second suture is a separate suture that is not part of any other suture of said method.

16. A method as set forth in claim 12, wherein said at least one suture portion of said second suture is completely embedded in said second portion of said first suture such that no portion of said at least one suture portion of said second suture is visible.

17. A method as set forth in claim 12, wherein said first portion of said first suture and said at least one suture portion of said second suture do not contact the outer member.

* * * * *